US005461133A

United States Patent [19]
Hammar et al.

[11] Patent Number: 5,461,133
[45] Date of Patent: Oct. 24, 1995

[54] STAIN-RESISTANT ELASTOMERIC ORTHODONTIC FORCE MODULE

[75] Inventors: W. James Hammar; Miriam D. Nave, both of St. Paul, Minn.

[73] Assignee: Minnesota Mining and Manufacturing Company, St. Paul, Minn.

[21] Appl. No.: 199,471

[22] Filed: Feb. 22, 1994

Related U.S. Application Data

[62] Division of Ser. No. 652,047, Feb. 7, 1991, Pat. No. 5,317,074.

[51] Int. Cl.$^6$ .............................. C08G 77/04; A61C 3/00; C08F 30/08
[52] U.S. Cl. .................. 528/10; 433/18; 433/20; 433/22; 433/23; 522/908; 526/279; 528/26
[58] Field of Search .................... 528/26, 10; 433/18, 433/22, 23, 20; 522/908; 526/279

[56] References Cited

U.S. PATENT DOCUMENTS

| | | | |
|---|---|---|---|
| 3,228,741 | 1/1966 | Becker | 351/160 |
| 3,504,438 | 4/1970 | Wittman et al. | 32/14 |
| 3,530,583 | 9/1970 | Klein et al. | 32/14 |
| 3,665,052 | 5/1972 | Saam et al. | |
| 3,712,877 | 1/1973 | Patel et al. | |
| 3,758,947 | 9/1973 | Kesling | 32/14 A |
| 3,876,654 | 4/1975 | Pattison | |
| 4,035,565 | 7/1977 | Apotheker et al. | 526/249 |
| 4,038,753 | 8/1977 | Klein | 32/14 E |
| 4,214,060 | 7/1980 | Apotheker et al. | 525/387 |
| 4,288,345 | 9/1981 | Ashby et al. | 252/431 R |
| 4,450,263 | 5/1984 | West | 526/249 |
| 4,523,408 | 6/1985 | Drisaldi et al. | 433/8 |
| 4,786,657 | 11/1988 | Hammar et al. | 522/90 |
| 4,818,225 | 4/1989 | Fasnacht | 433/18 |
| 4,828,117 | 5/1989 | Panzera et al. | 206/63.5 |
| 4,863,977 | 9/1989 | Tateosian et al. | 525/77 |
| 4,867,679 | 9/1989 | Rackley | 433/15 |
| 4,882,390 | 11/1989 | Grootaert et al. | 525/326.3 |
| 4,933,418 | 6/1990 | Sterrett | 528/76 |
| 4,946,387 | 8/1990 | Adell | 433/20 |
| 4,950,158 | 8/1990 | Barngrover et al. | 433/11 |
| 5,317,074 | 5/1994 | Hammar et al. | 528/44 |
| 5,378,146 | 1/1995 | Sterrett | 433/11 |

OTHER PUBLICATIONS

"Description of Kraton Rubbers", Shell Chemical Co., SC:198–89 pp. 1–13.
"Thermoplastic Elastomers, A Comprehensive Review" (pp. 13–46) Chapter 2 and pp. 92–116 and 133–142.
"Silicones As Biomaterials", Quinn and Courtney, British Polymer Journal 20 (1988) pp. 25–32.
"The Chemistry of Silicone Materials for Biomedical Devices and Contact Lenses", Whitford, 7–82, Biomaterials 1984, vol. 5 Sep.
"New Generation Silicones for Medical Devices", Arkles, MD&DI Apr. 1981 pp. 31–35, 60–61.
"Look What You Can Make Out of Silicones", Arkles, Chemtech Sep. 1983, pp. 542–555.
"Fluorinated Elastomers", West & Holcomb pp. 500–515.
"Polyphosphazens: New Polymers with Inorganic Backbone Atoms", Allcock, Science, Sep. 1976, pp. 1214–1219.
"Elastomers in Biomedical Applications: An Overview of Types and End–Uses", McMillin, Elastomerics, Nov. 1988, pp. 22–27.
"Principles of Color Technology", Billmeyer, Jr., Saltzman; Second Edition, J. Wiley & Sons 1981.
"Processing and Fabricating Kraton Thermoplastic Rubber Compounds", Shell Chemical Company (No. SC:455–81).
Lelah et al., *Polyurethane in Medicine*, CRC Press, Inc., pp. 27–30 (1986).
Kirk–Othmer, Encyclopedia of Chemical Technology, Third Edition, vol. 23, "Urethane Polymers", pp. 576, 577, 584, 585, 587.

*Primary Examiner*—James J. Seidleck
*Assistant Examiner*—John M. Cooney, Jr.
*Attorney, Agent, or Firm*—Gary L. Griswold; Walter N. Kirn; James D. Christoff

[57] ABSTRACT

An elastomeric orthodontic device such as a ligature, rotation wedge or force module is made of a composition selected from one or more classes of materials, such that the device has certain physical properties useful for orthodontic treatment and also is resistant to staining by common foods and beverages such as mustard, tea and coffee.

29 Claims, 1 Drawing Sheet

STAIN-RESISTANT ELASTOMERIC ORTHODONTIC FORCE MODULE

This is a division of application Ser. No. 07/652,047 filed Feb. 7, 1991 now U.S. Pat. No. 5,317,074.

BACKGROUND OF THE INVENTION

1. Field of the Invention

This invention relates to an elastomeric orthodontic device (such as a ligature) that is resistant to staining.

2. Description of the Related Art

Orthodontic treatment normally involves the application of mechanical forces to urge improperly positioned teeth into correct alignment. One common form of orthodontic treatment includes the use of orthodontic brackets that are fixed to teeth. A resilient curved arch wire, seated in slots of the brackets, is bent or twisted at strategic locations. The restoring force exerted by the arch wire tends to shift the teeth into orthodontically correct alignment.

Various types of elastomeric devices, also known as force modules, are used in orthodontic treatment. For example, tiny O-ring devices are used as ligatures to secure the arch wire in slots of the brackets. Elongated devices, including chain-like modules having a number of interconnected O-ring portions, may be stretched between selected brackets in order to move certain teeth relative to other teeth. Other devices are especially adapted to separate adjacent teeth or to rotate a tooth about its long axis. Examples of such devices can be found in U.S. Pat. Nos. 3,530,583, 3,758,947, 4,038,753 and 4,950,158.

Elastomeric devices for orthodontic use are often clear in color when new, and present a satisfactory appearance when first installed in the mouth next to metallic or ceramic brackets and metallic archwires. However, unlike most brackets and archwires, conventional elastomeric devices quickly stain when exposed to foods or beverages such as mustard, tea, and coffee. Mustard, in particular, has been known as a stain agent that is difficult to resist. Brushing the teeth or rinsing the mouth normally does not remove the stain, and the unsightly appearance persists until the devices are replaced. Discoloration is particularly noticeable when the brackets are made of translucent ceramic and assume the color of the underlying tooth.

U.S. Pat. No. 4,933,418 indicates that a particular crosslinked polyurethane orthodontic device made using polycaprolactone is more resistant to staining by mustard than devices made of other mentioned materials. However, there is a continuing need in the art to provide elastomeric orthodontic devices that are more resistant to staining than the devices known in the past, in order to improve the appearance of the device in the mouth as much as feasible. Elastomeric orthodontic devices should also permit substantial elongation before rupture, be resistant to tearing, and provide satisfactory resistance to force degradation over extended periods of time.

SUMMARY OF THE INVENTION

The present invention is directed toward a stain-resistant elastomeric orthodontic device that is sufficiently free of hydrocarbon-based polyether segments and hydrocarbon-based polyester segments to provide resistance to staining. The device is made of a material having per 2 mm thickness a Hunter color difference when using a 2.5 cm illuminated opening of (a) less than 40 when compared to a Hunter white standard tile and (b) less than 33 after immersion in mustard solution for 30 minutes when compared to the material before immersion in mustard solution.

DETAILED DESCRIPTION OF THE PREFERRED EMBODIMENT

Figure 1:
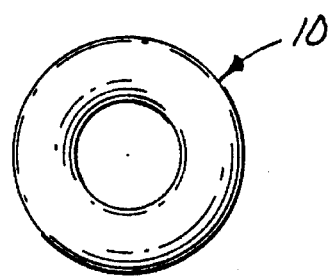
FIG. 1 is a side elevational view of an orthodontic ligature device that is made in accordance with one embodiment of the invention.

The stain-resistant orthodontic device of the present invention is made of a material selected from groups of certain elastomers that have been found to resist staining by common foods and beverages. The selected elastomers also possess certain physical properties necessary for satisfactory use in orthodontia. As used herein, "elastomer" means a natural or synthetic polymer which at room temperature can be repeatedly stretched to at least twice its original length and which, after removal of the tensile stress, will quickly and forcibly return to approximately its original length.

Orthodontic elastomeric devices are often called "force modules" because the resilient force of the device in tension or compression is used to move a tooth or an orthodontic appliance relative to other teeth or orthodontic appliances. Consequently, the force exerted by the device when in tension or compression and the ability to be stretched without breakage are important physical properties. Preferably, the material of the device can be stretched without breakage to at least 150% elongation, more preferably to at least 300% elongation and most preferably to at least 400% elongation, and has a tensile strength of greater than 2.0 MPa at 300% elongation, and more preferably greater than 4.0 MPa at 300% elongation. Preferably, the tensile strength of the material at 300% elongation is less than 30 MPa and more preferably less than 20 MPa. The tensile strength preferably does not degrade to a value less than 1.5 MPa at 300% elongation during a two-year shelf life in the atmosphere plus an expected time of 1–3 months that the device is used in the mouth.

It is believed that moisture uptake by the elastomer may adversely affect mechanical properties and long-term stability due to hydrolysis of the polymer backbone; consequently, the weight gain of the device due to moisture uptake should not render the device unsuitable for use during orthodontic treatment. Preferably, the weight gain of the material due to moisture uptake is less than 1.2% by weight, and more preferably less than 1.0% by weight. Also, the material should be tasteless, odorless and non-toxic.

The present invention is preferably made of a material that is initially colorless or relatively light in color so that the device presents a satisfactory appearance when placed in use. Per 2 mm thickness, the material when compared to a Hunter white standard tile has a Hunter color difference when using a 2.5 cm illuminated opening of less than 40, preferably less than 30, and more preferably less than 20. Within these ranges, the device may be either transparent, translucent or opaque.

Additionally, the material is resistant to staining by common foods and beverages such as mustard so that the device remains aesthetically pleasing in appearance and does not unduly darken or turn yellow during the time that the device remains in the oral cavity. Per 2 mm thickness, the material has a Hunter color difference when using a 2.5 cm illuminated opening of less than 33, preferably less than 20, and more preferably less than 10 after immersion in mustard solution for 30 minutes when compared to the material before immersion in mustard solution.

By comparision, some materials used for making conventional orthodontic ligatures have a relatively dark initial color that is believed to mask the effects of mustard staining. For example, the material for making ALASTIK A1 grey colored ligatures (3M Unitek Corp.) has a Hunter color difference per 2 mm thickness when using a 2.5 cm illuminated opening of 41.2 when compared to a Hunter white background tile, and of 5.23 after immersion in mustard solution for thirty minutes when compared to the material before immersion in mustard solution. However, ligatures that are somewhat lighter in initial color are often desired, especially when used in conjunction with miniature brackets or brackets made of a translucent material.

A first class of materials suitable for the present invention includes thermoplastic rubber polymers such as those commercially available under the trademark KRATON from Shell Chemical Company. The elastomers are di-block or tri-block copolymers having a rubbery phase and a glassy phase. Preferably, the polymers to be used in the present invention are the tri-block A-B-A type copolymers with the elastomeric block ("B") in the center and thermoplastic block ("A") on each end. The thermoplastic block or glassy phase is provided by a component having a hard character, such as styrene or alpha-methyl styrene, and is preferably made from monomers wherein the corresponding homopolymer has a $T_g$ greater than about 90° C. The elastomeric block or rubbery phase significantly affects the physical properties of the elastomer and is preferably selected from butadiene, isoprene, ethylene/butylene, polyisobutylene or the like. The rubbery phase is preferably made from monomers wherein the corresponding homopolymer has a $T_g$ less than about 10° C. Typically, the rubbery phase of the polymer constitutes between about 15–40% by weight of the total polymer. These copolymers are known to have low moisture uptake (see "KRATON Thermoplastic Rubber", published by Shell Chemical Company, no. SC:198–89), but their stain resistance to foods and beverages is unreported.

An example of a di-block copolymer is styrene-isoprene (Shell no. D1320X). Examples of tri-block copolymers include styrene-butadiene-styrene (D1102 and D2103) and styrene-ethylene/butylene-styrene (G1652, G2701X, G270X, G2706X and G2712X) block copolymers. Copolymers with butadiene or isoprene midblock can be further stabilized by crosslinking with peroxides or actinic radiation, optionally in the presence of olefinic additives such as acrylates, methacrylates and ethylene propylene dimer rubbers. The styrene-ethylene/butylene-styrene copolymer is particularly preferred because the midblock is saturated and tends to provide a stable material upon aging. The G1652 copolymer is preferably modified with polypropylene and/or mineral oil (which could result in a material similar to G2703X).

A second class of materials suitable for use in the present invention includes polyurethanes, polyureas and polyurethane/ureas. These materials can be thermoplastic materials or crosslinked by heat or actinic radiation to provide set materials. Polyurethanes and polyurethane/ureas are disclosed in U.S. Pat. No. 4,786,657 (see also *Thermoplastic Elastomers, A Comprehensive Review*, edited by N. R. Legge, G. Holden and H. E. Schroeder, Hanser Publishers, New York, 1987, p. 13–46). As used herein, "hard segment" means the amount of isocyanate, chain extender, small glycol and/or small diamine, and "soft segment" means the amount of macrodiol and/or macrodiamine. Also, "chain extender" or "small glycol" or "small diamine" means a low number average molecular weight (<400) diol or diamine, respectively, and "macrodiol" or "macrodiamine" means a high number average molecular weight ($\geq$400) diol or diamine, respectively. The isocyanate is preferably an aromatic or aliphatic di- or triisocyanate and most preferably an aliphatic diisocyanate.

At least about 70% of the soft segment is preferably polybutadiene, isoprene, polyisobutylene or saturated analogs thereof, and more preferably is polybutadiene or a saturated analog thereof, such as hydrogenated polybutadiene. Preferably, polyethers and/or polyesters should not comprise more than about 30% by weight of the soft segment in order to impart satisfactory stain resistance and low moisture uptake. The hard segment is preferably less than about 60% by weight and more preferably less than about 50% by weight of the polyurethane, polyurea or polyurethane/urea. Adherence to the preferred hard/soft segment compositions and proportions provides moisture uptake equal to or less than that of conventional elastomeric orthodontic devices. Because there is less hydrocarbon-based polyether and hydrocarbon-based polyester in the soft segment of the device as compared to conventional devices, less weight gain is observed and the tensile strength of the present invention is normally not unduly affected when exposed to fluids in the oral cavity. Preferably, the moisture uptake is less than about 1.2% by weight and more preferably less than 1.0% by weight.

A third class of materials suitable for use in the invention includes silicone materials, which preferably are selected from (1) crosslinked silicone elastomers, (2) α-methyl styrene-silicone-α-methyl styrene block copolymers of the type ABA, ABAB or (AB)$_n$ in a star (where "A" is the thermoplastic block and "B" is the elastomeric block), and (3) silicone polycarbonate block copolymers of the type ABAB. Crosslinked silicone elastomers are available from Petrarch Systems, Inc., while the styrene block copolymers are available from Dow Chemical Co. Silicone polycarbonates are available from General Electric.

A fourth class of materials suitable for this invention includes α-olefin thermoplastics such as ethylene propylene dimer (EPDM) rubbers and ethylene propylene monomer (EPM) rubbers. The hydrocarbon backbone of both types of rubbers appears to impart stain resistance to these materials. These ,materials preferably contain from 30–100 weight percent of EPDM or EPM rubbers that are preferably non-oil-extended. ("Non-oil-extended" refers to a rubber in which no oil was added during polymerization.)

Many commercially available EPDM or EPM rubbers can be used. The preferred rubber is NORDEL 1470, a non-oil-extended EPDM rubber (E. I. du Pont de Nemours & Co.). Examples of oil-extended EPDM rubbers are POLYSAR XC-955 (Polysar Inc.), and EPSYN P597 (Copolymer Co.), both of which contain 50 weight percent of paraffinic oil or naphthenic oil. Other commercially available oil-extended rubbers include EPSYN P557 and EPSYN P558 (Copolymer Co.), and VISTALON 3666 (Exxon Corp.).

The EPDM and EPM rubber materials preferably include a processing oil to soften the resultant device. Preferably, about 10 to 30 weight percent of processing oil is added to the mixture. Examples of oils include paraffinic oil, naphthenic oil, and vegetable- or animal-derived oils.

The EPDM or EPM rubber materials may also include hydrated or precipitated silica or fumed silica to reinforce the molded device. The percentage of silica preferably is about 2 to 70 weight percent, and more preferably is about 4 to 30 weight percent. Examples of suitable silicas are CAB-O-SIL M7 (Cabot Corp.) and HISIL 233 and HISIL 210 (PPG Industries).

Polymeric plasticizers in a liquid state may be added to the EPDM or EPM rubber mixture to increase its workability. The amount of plasticizer added varies with the viscosity of the polymer, and preferably ranges up to about 30 weight percent, and more preferably 3 to 10 weight percent of the mixture. When a plasticizer is desired, preferably a polybutene, such as INDOPOL (Amoco), and a liquid EPDM, such as TRILENE (Uniroyal Chemical), are used.

Preferably, 5 to 15 weight percent of an extender is used in the EPDM or EPM rubber materials in order to increase the mechanical elongation of the cured composition. Extenders that are believed to be suitable include aluminum trihydrate, clay, talc, kaolin, mica, calcium carbonate, magnesium carbonate, aluminum silicate and magnesium silica.

The EPDM and EPM-rubber materials may also include a colorant such as titanium dioxide to whiten the cured composition. The amount of colorant preferably ranges from 0 to 20 percent by weight. Other additives that are believed to be suitable include antioxidants, organic silanes, powdered acrylics, zinc oxide and magnesium oxide, along with sur face-treated, precipitated and hydrated variations of the same.

The EPDM or EPM rubber materials may be cured by a curing agent such as a peroxide or by exposure to actinic radiation (such as UV) to increase the tensile strength of the resultant device. The preferred method of cure utilizes a per oxide curing agent such as dicumyl peroxide, 1,1-di(t-butyl peroxy)cyclohexane, 2,5-dimethyl-2,5-di(t-butylperoxy)hexane, 3-ethyl-3,3-di(t-butylperoxy) butyrate, 1,1-bis(t-butylperoxy),3,3,5-trimethyl cyclohexane, 2,5-dimethyl-2,5-bis(t-butylperoxy)hexane, t-butyl cumyl peroxide, $\alpha,\alpha'$-bis(t-butylperoxy)diisopropylbenzene, or n-butyl, 4,4-bis(t-butylperoxy)valerate.

The optimum amount of peroxide depends on the specific peroxide used, the combination of polymeric materials, the acidity of the extenders and the amount of processing oil. EPDM rubbers may require different amounts of curative (peroxide) to yield the same degree of crosslinking. The most preferred peroxide is dicumyl peroxide in the range of 1 to 5 weight percent.

A fifth class of materials suitable for the invention includes fluoroelastomers including three basic types, namely fluorocarbon, fluorosilicone and fluoroalkoxyphosphazene. Examples of commercial fluorocarbon elastomers include poly(vinylidene fluoride-co-hexafluoropropylene) (FLUOREL, 3M), poly(vinylidene fluoride-co-hexafluoropropene-co-tetrafluoroethylene) (VITON B; E. I. du Pont de Nemours & Co.) and poly(vinylidene fluoride-co-hexafluoropropylene-co-tetrafluoroethylene) (plus cure-site monomer) (VITON G, E. I. du Pont de Nemours & Co.). The fluorosilicone elastomers have repeating units of the general formula

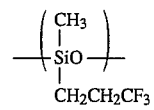

and contain small amounts of

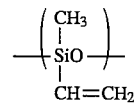

used for crosslinking with peroxides. Suitable formulations for fluorosilicone elastomers comprise about 10–90 parts per hundred resin (phr) methyl trifluoropropyl silicone, 10–90 phr silica based fillers, 1–50 phr metal oxide fillers and 1–10 phr silane fluids. The polyfluoroalkoxyphosphazenes are a recent commercial addition to the fluorinated elastomer family, and are vulcanizable by peroxide via incorporation of a cure-site monomer.

Fluoroelastomers are disclosed in U.S. Pat. Nos. 3,712,877, 3,876,654, 4,035,565, 4,214,060, 4,450,263 and 4,882,390. Fluoroelastomers are also described in West, A. C. and Holcomb, A. G., "Fluorinated Elastomers," Kirk-Othmer, *Encyclopedia of Chemical Technology*, Vol. 8, pp. 500–515 (3rd edition, John Wiley & Sons, 1979). Suitable fluoroelastomer formulations include fillers such as titanium dioxide to impart an aesthetic tooth-like color and also provide satisfactory physical properties such as tensile strength, elongation at break, and compound flow (compound flow properties are an important parameter in molding goods of small or complex shape).

The materials of the present invention may be formulated by selectively blending certain combinations of the materials set out in one or more of the classes above and can contain conventional adjuvants such as chemical or photochemical polymerization initiation systems, accelerators, inhibitors, stabilizers, viscosity modifiers (including waxes, extending oils or elastomeric gums) toughening agents (such as polypropylene), surface tension modifiers, wetting aids, antioxidants and extending or reinforcing fillers (such as fumed silica or zinc oxide). The materials can also include colorants such as dyes or pigments (e.g., $TiO_2$) in instances where the initial color of the molded device is darker than desired or otherwise unsatisfactory. In some instances, the initial color of the molded device may be lightened by varying the molding conditions and ensuring that the vessels used during mixing are free of contaminants. Depending upon the material selected, orthodontic devices may be made by extrusion, injection molding, liquid injection molding, compression molding, or reaction injection molding.

The presently preferred material of the invention is the KRATON G2703X thermoplastic rubber polymer. This material is injection molded into orthodontic devices such as the ligature assembly described in U.S. Pat. No. 4,038,753 using an ARBURG injection molding machine (Model "Allrounder 220E/150") with the following conditions: injection speed setting 5.0, nozzle power setting 35%, screw speed 360 rpm, back heater 180° C., front heater 205° C., 50 kg/cm² pressure, 22 seconds total molding time, 14 seconds injection and hold time. Other possible processing conditions are set out in "Processing and Fabricating KRATON Thermoplastic Rubber Compounds" published by Shell Chemical Company.

Referring now to the drawings, FIG. 1 illustrates a ligature or tensioning device 10 that can be made of the materials set out above. The annular device 10 has a circular cross-section, and resembles an O-ring. In use, the device 10 is stretched around tie wings of an orthodontic bracket and over an arch wire, in order to ligate the wire to the bracket and urge the wire toward a fully seated orientation in the bottom of a slot formed in the bracket.

Although not shown, the stain-resistant materials set out above may also be used to make a tooth separator device that is similar to but larger in size than the device 10 shown in FIG. 1. In use, the tooth separator device is placed between selected teeth to urge the teeth apart and provide a space for subsequent installation of a metal band. The band may serve as a base for a bracket or, if placed on the molars, serve as a base for a buccal tube which receives the end of the arch wire.

Figure 2:
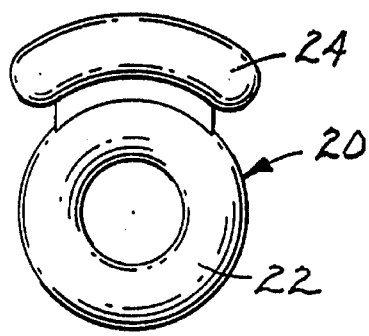
FIG. 2 is a side elevational view of a ligature device according to another embodiment of the invention.

FIG. 2 illustrates another orthodontic ligature device 20 which has an annular portion 22 that is similar in shape to the device 10. However, the device 20 also includes a bumper portion 24 such as described in U.S. Pat. No. 4,950,158. The bumper portion 24 extends over occlusal surfaces of the bracket in order to hinder direct contact of the bracket with an opposing tooth.

Figure 3:
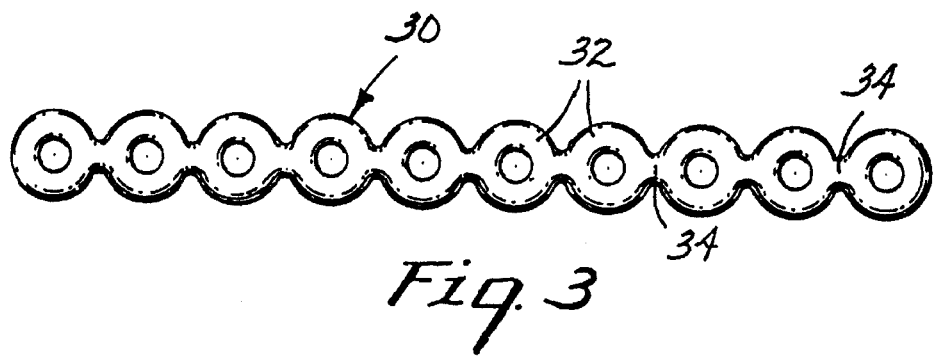
FIG. 3 is a side elevational view of a chain-like device made in accordance with another embodiment of the invention.

An elongated, chain-like tensioning module device 30 as shown in FIG. 3 is also made of the stain-resistant materials set out above, and has a number of annular portions 32 that are interconnected by bridging portions 34. Each annular portion 32 is similar in configuration to the ligature device 10 shown in FIG. 1. In use, the device 30 is cut to an appropriate length. Next, some or all of the annular portions 32 are placed around tie wings of selected brackets in order to ligate the wire to those brackets. If the device 30 is in longitudinal tension, the teeth having brackets ligated by the device 30 will tend to move toward each other.

Figure 4:
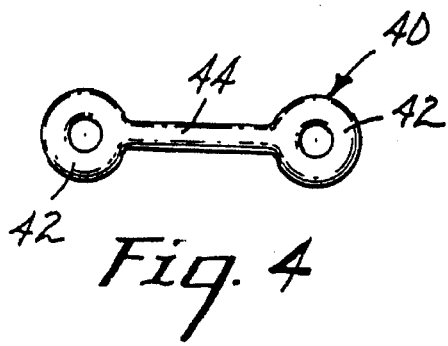
FIG. 4 is a side elevational view of an elongated device made in accordance with yet another embodiment of the invention.

FIG. 4 illustrates an integrally molded elongated tensioning device 40 that is also made of the stain-resistant materials set out above. The device 40 has opposed annular end portions 42 similar in configuration to the device 10. The end portions 42 are interconnected by a flexible, somewhat cylindrical shaft portion 44. The annular portions 42 function to ligate the arch wire to appropriate brackets. The shaft portion 44, when placed in tension, urges the brackets connected to the annular portions 42 toward each other.

Figure 5:
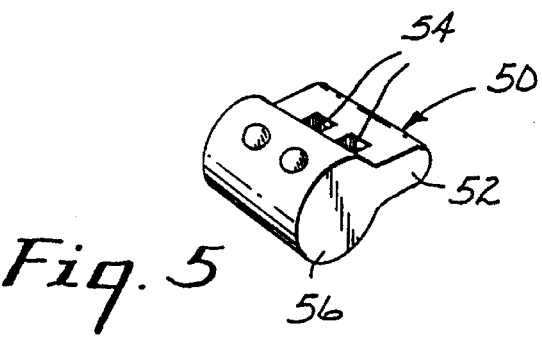
FIG. 5 is a perspective view of an orthodontic rotation wedge device according to another embodiment of the invention.

An integrally molded orthodontic rotation wedge device 50 is depicted in FIG. 5; and has a base 52 with two apertures 54 adapted to be placed over tie wings of a selected bracket. A somewhat cylindrical wedge portion 56 is placed in compression between the arch wire and adjacent surfaces of the tooth, and serves to rotate the tooth about its long axis.

SAMPLE PREPARATION

Elastomeric materials of the invention were pressed into thick or thin films for testing. Thin films were made in mold assemblies named "A" and "B" by placing a sufficient amount of polymer (25–30 grams) in the mold assembly to fill the mold cavity. Mold assembly A had a 30.5 cm ×30.5 cm ×0.6 cm thick aluminum base plate with a central 20 cm ×20 cm ×0.5 mm deep polymer-receiving mold cavity and a 0.6 cm wide ×1.3 mm deep overflow groove extending around the periphery of the mold cavity at a distance 0.6 cm away from the latter. The mold cavity was treated with a mold release agent (RAM 225, RAM Products), filled with polymer, covered with a sheet of polyester film (SCOTCH-PAK no. 1022, 3M) and and then covered with a 30.5 cm ×30.5 cm ×0.6 cm thick aluminum top plate.

Mold assembly B had a 30.5 cm ×30.5 cm ×0.3 cm thick aluminum base plate covered by a sheet of the polyester film. Spacer strips (1.3 to 1.9 cm wide and 0.4 mm thick) were arranged on the film to form one, two or four polymer-receiving mold cavities. After filling each cavity with polymer, another sheet of polyester film was placed on top of the spacers and was covered by a 30.5 cm ×30.5 cm ×0.3 cm thick aluminum top plate.

Thick films were made in a mold assembly named "C" that included a 30.5 cm ×30.5 cm ×0.6 cm thick aluminum base plate having four 10.1 cm ×10.1 cm ×2 mm polymer-receiving cavities that had been treated with the mold release agent. A 3 mm wide ×4 mm deep groove extended around the periphery of each cavity at a distance 3 mm from the latter. The cavities were arranged in two rows of two in the base plate with a distance of 3.8 cm between the grooves of adjacent cavities and a distance of 1.8 cm between the edge of the base plate and adjacent grooves. A sufficient amount of polymer (30–35 grams) was placed in each cavity to fill the latter. The base plate was covered with a sheet of the polyester film and then covered with a 30.5 cm ×30.5 cm ×0.6 cm thick aluminum top plate.

The selected mold assembly was then inserted between two 1 mm thick pieces of cardboard and two 13 mm thick steel plates, and placed between preheated platens (10 cm diameter ram) of a hydraulic press (unless otherwise indicated, Wabash Metal Products, Inc. press model 20-12-2TM2WCB). After operation of the press, the resultant films were visually checked to ensure that each film had a consistent, smooth appearance without irregularities such as bubbles or visible pellet-like features. (If irregularities appear, molding temperatures, pressures and/or times can be increased to yield a film with the desired appearance. If the films are darker than expected, the molding temperatures, pressures and/or times can be decreased).

SAMPLE TESTING

At least five samples of each polymer film were tested for mechanical properties. Samples made using mold assemblies A or B were about 1.3 cm ×10 cm ×0.5 mm thick, while samples made using mold assembly C were either about 0.6 cm ×10 cm ×2 mm thick or 0.3 cm ×10 cm ×2 mm thick. Each sample was tested using an MTS 880 material test system (MTS Systems Corporation, Minneapolis, Minn.) equipped with a 227 kg load cell and pneumatic grips lined with thin rubber. The initial grip separation was 2 cm and the grips moved apart at a rate of 25.4 cm/min to a maximum separation of 25.4 cm. The tensile strength at 300% elongation (i.e., four times its normal length), tensile strength at break and percent elongation at break for the average of five samples was noted. (For samples that did not break during the tensile test, the tensile strength at the maximum elongation attained and the maximum elongation values (along with the notation ">") are recorded in the columns below entitled tensile at break and elongation at break respectively.)

For testing of initial color and stain resistance to mustard, each polymer was molded into a film using mold assembly C and press conditions similar to the conditions that were used for molding the corresponding polymer film used in mechanical tests. Samples of about 3.2 cm ×3.2 cm ×2 mm were cut from each film.

The determination of the initial color was carried out by first standardizing a Hunter Lab Scan 6000 Spectrocolorimeter instrument (Hunter Associates Laboratory, Reston, Va.) against a white Hunter background standard tile (Part no. LS-13553) of the instrument using a 2.54 cm diameter illuminated opening. Next, a sample of each film was placed in front of the illuminated opening. Three color determinations were taken at random locations on the sample and averaged. A Hunter color difference measurement (referred to as "Color difference before/background") represents the difference in initial color of the sample as compared to the white standard tile, and was calculated according to the CIELAB 1976 L*a*b, color difference equation set out in Billmeyer & Saltzman, *Principles of Color Technology* (Interscience Publishers, New York, copyright 1981) p. 103. A larger "Color difference before/background" value indicates that the sample had a darker initial color.

For testing of the stain resistance of each polymer to mustard, a second sample of each film was immersed in a mustard solution (80% by weight French's 100% pure prepared yellow mustard Lot no. M90157-14, 20% by weight water) for thirty minutes at room temperature, at which time it was removed, rinsed thoroughly with water, blotted dry and tested to determine any change in degree of yellowness according to ASTM method D 1925, using the Hunter Spectrocolorimeter and a 2.54 cm diameter illuminated opening. "Yellowness index after" was calculated by determining the average of the yellowness index at three random locations on the sample after immersion in the mustard solution. A higher yellowness index number indicated a sample having a stronger yellow color. "Yellowness Index before" was calculated by determining the average of the yellowness index at three random locations on the unimmersed sample.

A second Hunter color difference determination (referred to as "Color difference after/before") was also calculated according to the CIELAB equation, and represents the difference in color of the immersed sample as compared to the unimmersed sample. Again, the color of each sample was determined by calculating the average of the color determined at three random locations on each sample. A smaller "Color difference after/before" value indicates that the sample was less susceptible to staining by mustard.

Weight gain due to moisture uptake was measured by preparing film samples which ranged in size from 50 $mm^3$ to 8 $mm^3$. The samples were placed in small vials of Ringer's solution (prepared by mixing 36 g NaCl, 1.69 g KCl, 0.95 g $CaCl_2$ and 0.8 g $NaHCO_3$ into 4 liters of deionized water), and the vials were sealed and stored in a 37° C. oven for 24 hours. The samples were then removed from the Ringer's solution, blotted dry with a paper towel and weighed to determine weight gain. The procedure was repeated until a constant final wet weight was achieved. The samples were then dried in a 70° C. oven for 24 hours and weighed to determine the final dry weight. The percent "Weight gain" was calculated using the following formula:

$$\% \text{ Weight Gain} = \frac{\text{Final wet weight} - \text{final dry weight}}{\text{Final dry weight}} \times 100$$

The following illustrative examples are offered to aid understanding of the present invention, and should not be considered as limiting its scope. Unless otherwise indicated, all parts and percentages are by weight and all molecular weights are number average molecular weights. Also, a dash ("–") in the following tables indicates that a value or measurement was not determined.

EXAMPLE 1

A thermoplastic styrene-ethylene/butylene-styrene rubber block copolymer (KRATON G2701X, Shell Chemical Co.) was injection molded into orthodontic ligatures using the ARBURG machine with the molding conditions previously described. The ligatures were similar to the ligature devices 10 shown in FIG. 1. Three ligatures were immersed in mustard solution as described in "SAMPLE TESTING" for 30 minutes. Three other KRATON ligatures were immersed for 24 hours in coffee at 45° C. made by using 20 grams of coffee (MAXWELL HOUSE RICH FRENCH ROAST, Maxwell House Coffee Co.) with 1 liter of water in an automatic drip coffeemaker (DIAL-A-BREW II, Norelco). Three other KRATON ligatures were immersed for 24 hours in tea at 45° C. (LIPTON ORANGE PEKOE and PEKOE CUT BLACK TEA, Thomas J. Lipton, Inc.) that was made by steeping one tea bag in 75 ml of water for five minutes at 90° C. The ligatures were rinsed thoroughly with water after removal from the mustard, coffee or tea and blotted dry. The three ligatures that had been immersed in mustard were mounted next to three unimmersed ligatures on the tacky side of a white Post-It note (3M) that was in turn mounted on a sheet of white bond paper (type 696, 3M). The mounting procedure was repeated for the ligatures immersed in coffee and tea.

The paper holding the mounted ligatures was secured at eye level to a hallway wall lighted with fluorescent light fixtures. Five individuals were asked to stand directly next to the ligatures, and then back up to determine the distance at which the difference in color between the immersed ligatures and the unimmersed ligatures was no longer perceptible.

For comparative purposes, ALASTIK A1 (0.3 cm outer diameter, 3M Unitek Corp.) and POWER 'O' 120 (lot #OE1, Ormco Corp.) ligatures were immersed in mustard, coffee and tea mixtures as described above and mounted next to corresponding unimmersed ligatures. Again, five individuals were asked to stand next to the mounted ligatures and walk away as described above until a difference in color between the immersed and unimmersed ligatures was no longer perceptible.

Table IA provides the average distance in meters (along with mean standard deviation) at which the five individuals could not perceive any difference in color between immersed and unimmersed ligatures for each food or beverage.

TABLE IA

| Run no. | Designation | Mustard | Coffee | Tea |
| --- | --- | --- | --- | --- |
| 1 | KRATON G2701X | 0 ± 0 | 2.83 ± 1.68 | 1.39 ± 0.59 |

TABLE IA-continued

| Run no. | Designation | Mustard | Coffee | Tea |
|---|---|---|---|---|
| Comparison 1 | ALASTIK A1 | 2.23 ± 1.65 | 10.98 ± 1.50 | 13.75 ± 1.73 |
| Comparison 2 | POWER 'O' 120 | 1.72 ± 1.14 | 8.39 ± 0.47 | 12.21 ± 1.68 |

The data show mustard, coffee and tea all severely stain the commercial ALASTIK A1 and POWER 'O' 120 ligatures. The KRATON G2701X ligatures were not visibly stained by mustard. Coffee and tea show only very slight staining of the KRATON G2701X ligatures.

Two KRATON thermoplastic rubber polymers of styrene-ethylene/butylene-styrene block copolymer type (G2701X and G2703X, Shell Chemical Co.), were injection molded into orthodontic ligatures and immersed in mustard as described in SAMPLE TESTING. For comparative purposes, ALASTIK A1 and POWER 'O' 120 ligatures were also immersed in mustard. Color difference was measured according to the "SAMPLE TESTING" procedure, except that four ligatures were mounted in a square pattern (two rows of two, with adjacent ligatures touching each other) on translucent double stick tape sold under the trademark SCOTCH (3M) that was mounted on the spectrocolorimeter's white standard tile. The illuminated opening was 0.6 cm in diameter. Four measurements were taken for each set of four ligatures, rotating the tile carrying the tape with the four ligatures 90° between each measurement.

Table IB sets out the yellowness index of the ligatures before and after immersion in mustard along with the color difference.

TABLE IB

| Run no. | Designation | Yellowness index before | Yellowness index after | Color difference after/before |
|---|---|---|---|---|
| 1 | KRATON G2701X | 5.12 | 7.79 | 1.59 |
| 2 | KRATON G2703X | 6.33 | 8.89 | 1.8 |
| Comparison 1 | ALASTIK A1 | 9.72 | 46.39 | 31.81 |
| Comparison 2 | POWER 'O' 120 | 6.6 | 45.1 | 31.55 |

The data show that the KRATON G2701X and G2703X ligatures are highly resistant to staining by mustard, while the ALASTIK A1 and POWER 'O' 120 ligatures are very susceptible to staining by mustard.

EXAMPLE 2

A thick film of at least one polymer from each class above was made in mold assembly "C" (under press conditions as reported in EXAMPLES 3–9 for each corresponding polymer) and cut into rectangular samples 1 cm ×3 cm ×2 mm thick. Samples of each film were immersed either in mustard solution as described in "SAMPLE TESTING", or in coffee or tea as described in EXAMPLE 1. Other samples of each film were immersed for 24 hours at room temperature in one of the following: cherry-flavored drink (Cherry Kool-Aid, General Foods Corp.) that was made by dissolving 84.23 g of drink powder in one liter of water, grape jelly (Flav-O-Rite, Preferred Products, Inc.) or blueberry pie filling (Flav-O-Rite, Preferred Products, Inc.).

Each immersed strip was placed on white bond paper (696, 3M) next to an unimmersed strip of the same formulation. The strips were then observed at a distance of 0.5 meters and rated on a scale of 0 to 4 wherein 0 indicated no visible staining and 4 indicated severe staining. The data provided below in Table IIA were scored based on the intensity of the stain (if any) relative to the original color of the staining agent. For example, blueberry pie filling is dark, but the samples exhibited only slight staining.

The procedure set out above was repeated for comparison purposes with two thermoplastic polyurethane films of materials that have previously been used for elastomeric orthodontic devices, namely a polyester polyurethane ("Comparison 1") and a polyether polyurethane based on an aliphatic diisocyanate ("Comparison 2"). The comparison films were obtained as pellets and pressed into films according to the procedure set out in EXAMPLE 3. The results are set out in Table IIA.

TABLE IIA

| Run no. | Designation | Mustard | Coffee | Tea | Cherry Kool-Aid | Grape jelly | Blueberry pie filling |
|---|---|---|---|---|---|---|---|
| 1 | Polyurethane[1] | 2 | 2 | 3 | 1 | — | 1 |
| 2 | Polyurethane[2] | 2 | 2 | 3 | 0 | — | 1 |
| 3 | Silicone Elastomers[3] | 1 | 0 | 0 | 1 | 0 | 1 |
| 4 | Thermoplastic Rubber[4] | 0 | 0 | 1 | 1 | 0 | 0 |
| 5 | EPDM Rubber[5] | 0 | 0 | 0 | 0 | 0 | 1 |
| 6 | Fluoroelastomer[6] | 0 | 0 | 0 | 0 | 0 | 0 |
| 7 | Polyester[7] | 4 | 4 | 4 | 0 | 0 | 3 |
| Comparison 1 | Polyester polyurethane[8] | 4 | 3 | 4 | 1 | 0 | 1 |

TABLE IIA-continued

| Run no. | Designation | Mustard | Coffee | Tea | Cherry Kool-Aid | Grape jelly | Blueberry pie filling |
|---|---|---|---|---|---|---|---|
| Comparison 2 | Polyether polyurethane[9] | 4 | 3 | 4 | 2 | 4 | 1 |

[1]Composition of EXAMPLE 3, Run no. 12.
[2]Composition of EXAMPLE 3, Run no. 17.
[3]Composition of EXAMPLE 6, Run no. 3.
[4]Composition of EXAMPLE 7, KRATON G2706X.
[5]Composition of EXAMPLE 8, Run no. 1.
[6]Composition of EXAMPLE 9, Run no. 5.
[7]HYTREL 4056 (E. I. du Pont de Nemours & Co.).
[8]TEXIN (Catalog no. 480-A, H-279-1000, Mobay Corp.).
[9]Catalog no. NJ-85A-56X5 Lot E999-01065 (Thermedics, Inc.).

The data show that mustard, coffee and tea severely stain the polyester polyurethane and polyether polyurethane comparison materials. Additionally, the polyester material (HYTREL 4056) was severely stained by mustard, coffee, tea and blueberry pie filling. The remaining materials show good resistance to staining to most, and in some cases all, of the common foods and beverages set out in Table IIA.

The films immersed in the various staining agents set out in Table IIA were also tested for color difference (compared to corresponding, unimmersed films) in accordance with the procedure set out in SAMPLE TESTING except that the diameter of the illuminated opening was 0.6 cm. The results are set out in Table IIB.

TABLE IIB

| | | Color difference after/before | | | | | |
|---|---|---|---|---|---|---|---|
| Run no. | Designation | Mustard | Coffee | Tea | Cherry Kool-Aid | Grape jelly | Blueberry pie filling |
| 1 | Polyurethane | 5.24 | 6.86 | 28.27 | 3.02 | — | 0.23 |
| 2 | Polyurethane | 3.65 | 7.22 | 27.91 | 1.08 | — | 0.83 |
| 3 | Silicone Elastomer | 1.95 | 2.64 | 1.29 | 1.73 | 0.2 | 0.44 |
| 4 | Thermoplastic Rubber | 0.84 | 1.63 | 1.96 | 0.54 | 1.03 | 0.12 |
| 5 | EPDM Rubber | 3.96 | 3.96 | 1.91 | 1.16 | 0.45 | 1.86 |
| 6 | Fluoroelastomer | 0.8 | 0.65 | 0.14 | 0.7 | 1.65 | 1.00 |
| 7 | Polyester | 24.87 | 37.02 | 45.77 | 1.1 | 2.51 | 14.87 |
| Comparison 1 | Polyester polyurethane | 23.28 | 30.05 | 60.61 | 3.83 | 0.49 | 4.52 |
| Comparison 2 | Polyether polyurethane | 27.54 | 28.1 | 68.8 | 3.06 | 9.91 | 3.54 |

Again, the data show that mustard, coffee and tea severely stain the polyester polyurethane and polyether polyurethane comparison materials and correlates with the results of Table IIA. Additionally, the polyester material (HYTREL 4056) was severely stained by mustard, coffee, tea and blueberry pie filling. The remaining materials show good stain resistance to most, and in some cases all, of the common foods and beverages set out in Table IIB.

EXAMPLE 3

Preparation of Thermoplastic Polyurethanes

Thermoplastic polyurethanes with varying percentages of hard and soft segments were prepared by placing the respective amounts of the diols listed in TABLE III in a vessel. 0.49 Percent each of two stabilizers TINUVIN 328 and TINUVIN 770 (both from Ciba-Geigy Inc.) and 0.10% 4-methoxyphenol ("MEHQ") were added to the vessel (except Run nos. 8, 9, 10, 35 and 40 where these ingredients were not employed). The vessels were sealed and placed in a 100° C. oven for 5 to 10 minutes or until the additives melted. Each vessel was removed from the oven and allowed to cool at room temperature. Next, the amount of methylene bis(4-cyclohexylisocyanate) listed in TABLE III was added, and the resulting mixture stirred until it was homogeneous. Then 0.13% dibutyltin dilaurate catalyst ("DBTDL", Alfa Inorganics, Inc.) was added to each vessel (except for Run nos. 29, 30, 34 and 39 where 0.15% COTIN 222 tin catalyst (CasChem) was employed). The reaction mixture was stirred until exotherm was observed and the viscosity of the mixture increased noticeably. The reaction mixture was then poured into a polytetrafluoroethylene-lined shallow aluminum pan and cured in a 100° C. oven for about 1 hour.

An additional diol was added to Run nos. 30–40. 8.33 Percent decane diol by weight of the total mixture was added to Run no. 30. Polyester diol TONE 2221 (molecular weight 1000, Union Carbide Corp.) was added to Run nos. 31, 32, 33, 34 and 35 in 3.20%, 6.40%, 12.80%, 19.20% and 64.76% by weight of the total mixture respectively. Polyether glycol TERATHANE 2000 (molecular weight 2000, E. I. du Pont de Nemours & Co.) was added to Run nos. 36, 37, 38, 39 and 40 in 3.20%, 6.40%, 12.80%, 19.19% and 64.69% by weight of the total mixture respectively.

The polyurethane/urea of Run no. 41 was prepared by combining in a vessel the amounts of poly(butadiene)diol and methylene bis(4-cyclohexylisocyanate) identified in Table III, 0.10% MEHQ, 0.49% each of TINUVIN 328 and TINUVIN 770, 0.11% DBTDL and 650 ml tetrahydrofuran. The reaction mixture was refluxed under a nitrogen atmosphere for 2 hours, then allowed to cool to room temperature. The mixture was then chain extended by the dropwise addition (over about 30 minutes) of 3.9% ethylene diamine dissolved in 75 ml isopropyl alcohol until the isocyanate peak in the infrared spectrum was no longer evident. The resulting polymer solution was poured into a polytetrafluoroethylene-lined shallow aluminum pan and the solvent was allowed to evaporate overnight. Residual solvent was evaporated in vacuo at 50° C.

The polyurethane/urea of Run no. 42 was prepared in the same manner as the polyurethane/urea of Run no. 41, except that the amounts of poly(butadiene)diol and methylene bis(4-cyclohexylisocyanate) that were employed are those set out in Table III. Also, chain extending was carried out with 2.87% ethylene diamine and 2.2% 1,4-butanediol in 75 ml isopropyl alcohol.

The silicone carbinol used to make the polyurethanes of Run nos. 43 and 44 was prepared by combining in a vessel equipped with a reflux condenser 350 parts dry toluene, 133 parts 11-trifluoroacetoxyundecene, 125 parts 1,1,3,3-tetramethyl disiloxane (Petrarch) and 0.5 parts divinyltetramethyl disiloxane platinum catalyst (prepared according to U.S. Pat. No. 4,288,345). This mixture was heated at 80° C. under a nitrogen atmosphere for 4 days. 160 Parts activated charcoal was added to the vessel and after 20 minutes the mixture was filtered through diatomaceous earth while still warm. The filtrate was concentrated on a rotary evaporator at 80° C. The crude yield of 168 parts was further concentrated under a vacuum of 0.2 mm Hg in an oil bath at 200° C. 30 Parts activated charcoal and 250 parts mixed hexanes were added to the residue. The resultant mixture was then filtered through diatomaceous earth and the filtrate was concentrated on a rotary evaporator to provide 1,3-bis (11-trifluoroacetoxyundecamethylene)tetramethyl disiloxane. Next, the following ingredients were combined in a vessel equipped with a temperature regulator, reflux condenser and mechanical stirrer: 24.3 parts of the 1,3-bis (11-trifluoroacetoxyundecamethylene)tetramethyl disiloxane, 206.7 parts octamethylcyclotetrasiloxane (Petrarch) and a mixture of 2 parts concentrated sulfuric acid and 2.3 parts activated charcoal. The resultant mixture was heated with stirring at 80° C. under a nitrogen atmosphere for 26 hours. The mixture was then filtered through diatomaceous earth, rinsing with toluene. The residue was dissolved in a total of 100 parts toluene. 100 Parts methanol saturated with ammonia was added to the toluene solution and stirred at room temperature for 2 hours. The volatiles were first removed on a rotary evaporator and then under 0.3 mm Hg vacuum. The molecular weight by nuclear magnetic resonance of the silicone carbinol was about 5,600.

The silicone carbinol-based polyurethane of Run no. 43 was prepared by combining in a vessel 58.59 parts silicone carbinol, 29.45 parts methylene bis(4-cyclohexylisocyanate), 0.10 parts DBTDL and 660 parts tetrahydrofuran. The reaction mixture was refluxed under a nitrogen atmosphere for 16 hours and, while still at reflux temperature, was chain extended by the dropwise addition of 11.85 parts 1,4-butanediol in 60 parts tetrahydrofuran. Residual solvent was evaporated in vacuo at 50° C.

The silicone carbinol-based polyurethane of Run no. 44 was prepared by combining in a vessel 34.93 parts silicone carbinol, 34.93 parts poly(butadiene)diol, 23.73 parts methylene bis(4-cyclohexylisocyanate), 0.11 parts DBTDL and 60 parts tetrahydrofuran. The reaction mixture was refluxed under a nitrogen atmosphere for 16 hours, and while still at reflux temperature, was chain extended by the dropwise addition of 6.2 parts 1,4-butanediol in 66 parts tetrahydrofuran. The solvent was evaporated in vacuo at 50° C.

Set out below in Table III are the type and amount of poly(butadiene)diol, the amount of 1,4-butanediol and methylene bis(4-cyclohexylisocyanate) and the ratio of hard segment to soft segment for each polyurethane.

TABLE III

| | Ingredients | | | | |
|---|---|---|---|---|---|
| | Diol | | | Methylene bis- | Ratio |
| | Poly(butadiene) | | 1,4- | (4-cyclohexyl- | Hard:soft |
| Run no. | Type | Amount (%) | butanediol (%) | isocyanate) (%) | Segment (%):(%) |
| 1 | PBD(1350)[1] | 74.09 | 2.69 | 22.01 | 25:75 |
| 2 | " | 69.15 | 4.19 | 25.45 | 30:70 |
| 3 | " | 63.97 | 5.77 | 29.04 | 35:65 |
| 4 | PBD(2000)[2] | 79.03 | 2.41 | 17.35 | 20:80 |
| 5 | " | 74.09 | 3.87 | 20.82 | 25:75 |
| 6 | " | 69.15 | 5.29 | 24.34 | 30:70 |
| 7 | " | 63.97 | 6.80 | 28.02 | 35:65 |
| 8 | " | 49.94 | 11.11 | 38.83 | 50:50 |
| 9 | " | 26.97 | 17.74 | 55.17 | 73:27 |
| 10 | None | None | 25.56 | 74.32 | 100:0 |
| 11 | PBD(G1000)[3] | 74.09 | 2.92 | 21.77 | 25:75 |
| 12 | " | 69.15 | 4.43 | 25.21 | 30:70 |
| 13 | " | 64.00 | 5.97 | 28.82 | 35:65 |
| 14 | PBD(GI-1000)[4] | 74.09 | 3.16 | 21.54 | 25:75 |
| 15 | " | 69.15 | 4.62 | 25.01 | 30:70 |
| 16 | " | 64.00 | 6.17 | 28.62 | 35:65 |
| 17 | PBD(G2000)[5] | 74.09 | 3.87 | 20.82 | 25:75 |
| 18 | " | 69.15 | 5.33 | 24.30 | 30:70 |
| 19 | " | 63.97 | 6.80 | 28.02 | 35:65 |
| 20 | PBD(GI-2000)[6] | 74.09 | 4.07 | 20.63 | 25:75 |
| 21 | " | 69.15 | 5.49 | 24.14 | 30:70 |
| 22 | " | 64.00 | 6.96 | 27.83 | 35:65 |
| 23 | PBD(G3000)[7] | 74.09 | 4.82 | 19.88 | 25:75 |
| 24 | " | 69.15 | 6.16 | 23.47 | 30:70 |
| 25 | " | 64.00 | 7.59 | 27.20 | 35:65 |

TABLE III-continued

| | Ingredients | | | Ratio |
|---|---|---|---|---|
| | Diol | | Methylene bis- | |
| | Poly(butadiene) | 1,4- | (4-cyclohexyl- | Hard:soft |
| Run no. | Type | Amount (%) | butanediol (%) | isocyanate) (%) | Segment (%):(%) |
|---|---|---|---|---|---|
| 26 | PBD(GI-3000)[8] | 74.09 | 5.10 | 19.60 | 25:75 |
| 27 | " | 69.15 | 6.44 | 23.20 | 30:70 |
| 28 | " | 63.97 | 7.86 | 26.95 | 35:65 |
| 29 | Butarez HTL[9] | 63.96 | 7.96 | 26.83 | 35:65 |
| 30 | PBD(2000) | 69.15 | 0.00 | 21.30 | 30:70 |
| 31 | PBD(G2000) | 60.77 | 6.68 | 28.13 | 35:65 |
| 32 | " | 57.57 | 6.56 | 28.25 | 35:65 |
| 33 | " | 51.17 | 6.32 | 28.49 | 35:65 |
| 34 | " | 44.80 | 6.10 | 28.71 | 35:65 |
| 35 | " | 0.00 | 4.48 | 30.76 | 35:65 |
| 36 | " | 60.77 | 6.80 | 28.02 | 35:65 |
| 37 | " | 57.57 | 6.80 | 28.02 | 35:65 |
| 38 | " | 51.17 | 6.80 | 28.02 | 35:65 |
| 39 | " | 44.79 | 6.77 | 28.05 | 35:65 |
| 40 | " | 0.00 | 6.73 | 28.49 | 35:65 |
| 41 | PBD(2000) | 69.16 | 0.00 | 25.74 | 30:70 |
| 42 | " | 68.72 | 2.23 | 24.99 | 30:70 |
| 43 | None | 0.00 | 11.85 | 29.45 | 40:60 |
| 44 | PBD(2000) | 34.93 | 6.21 | 23.73 | 30:70 |

[1]1,350 M.W. hydroxyl-terminated poly(butadiene) (Polysciences Inc.).
[2]2,000 M.W. hydroxyl-terminated poly(butadiene) (Polysciences Inc.).
[3]1,000 M.W. hydroxyl-terminated) poly(butadiene) (Nissho Iwai American Corp.).
[4]1,000 M.W. hydroxyl-terminated hydrogenated poly(butadiene) (Nissho Iwai American Corp.).
[5]2,000 M.W. hydroxyl-terminated poly(butadiene) (Nissho Iwai American Corp.).
[6]2,000 M.W. hydroxyl-terminated hydrogenated poly(butadiene) (Nissho Iwai American Corp.).
[7]3,000 M.W. hydroxyl-terminated poly(butadiene) (Nissho Iwai American Corp.).
[8]3,000 M.W. hydroxyl-terminated hydrogenated poly(butadiene) (Nissho Iwai American Corp.).
[9]4,500 M.W. hydroxyl-terminated poly(butadiene) (Phillips Petroleum Co.).

The formulations of TABLE III were pressed into films. Runs 1–28 were made with mold assembly B, runs 29 and 30 were made with mold assembly A and runs 31–44 were made with mold assembly C. For runs 1–3, the press platens were held at 165° C. for 1 minute at a force (as indicated by the press) of 1,000 kg, 2 minutes at the same temperature and at a force of 4500 kg, 8 minutes at the same temperature and at a force of 11,000 kg, and then cooled to room temperature for about 8 minutes at a force of 11,000 kg. Cooldown was carried out by circulating tap water through the platens. For runs 1–3 only, this procedure was repeated two or three times in order to obtain a bubble-free film.

The pressing procedure for the remaining runs of EXAMPLE 3 was similar to the procedure for Run nos. 1–3 except that the press conditions were as follows: for run nos. 4–7, 160° C. at 1,000 kg for 1 minute, 4500 kg for 2 minutes, 9000–11,000 kg for 5–6 minutes, then cooldown at 9000–11,000 kg for 8 minutes. For runs 8–9, 160° C. at 1,000 kg for 3 minutes, 9,000 kg for 5–6 minutes, then cooldown at 9000 kg for 8 minutes. For run 10, 170° C. at 1,000 kg for 3 minutes, 11,000 kg for 5–6 minutes, then cooldown at 11,000 kg for 8 minutes. For runs 11–18, 20–24 and 26–27, 165° C. at 1,000 kg for 1 minute, 4500 kg for 2 minutes, 11,000 kg for 8 minutes, then cooldown at 11,000 kg for 8 minutes. For runs 19, 25 and 28, 160° C. at 1,000 kg for 1 minute, 4500 kg at 2 minutes, 9000–11,000 kg for 5–6 minutes, then cooldown at 9000–11,000 kg for 8 minutes. For run 29, 180° C. at 1,000 kg for 3 minutes, 11,000 kg for 8 minutes, then cooldown at 11,000 kg for 8 minutes. The pressing procedure for runs 30 and 41–44 was the same as the procedure for run 29 except that the platen temperature was 165° C. For runs 31–33, 35–38 and 40, the pressing procedure was the same as for run 29 except that the platen temperature was 190° C. For runs 34 and 39, 180° C. at 1,000 kg for 3 minutes, 11,000 kg for 10 minutes, then cooldown at 11,000 kg for 8 minutes.

For comparative purposes, the thermoplastic polyurethane comparison materials set out as Comparison 1 and Comparison 2 in EXAMPLE 2 were obtained as pellets and pressed into films. The polyester polyurethane film (Comparison 1) was made using mold assembly B with the following press conditions: 200° C. at 1,000 kg for 3 minutes, 11,000 kg for 10 minutes, then cooldown at 11,000 kg for 8 minutes. The polyether polyurethane film (Comparison 2) was made using mold assembly B with press conditions of 160° C. at 1,000 kg for 3 minutes, 11,000 kg for 8 minutes, then cooldown at 11,000 kg for 8 minutes.

The films of Run nos. 1–44 and Comparison 1–2 were cut into strips according to the procedure of SAMPLE TESTING and tested for tensile strength at 300% elongation, tensile strength at break, and elongation at break. The results are provided in TABLE IV along with weight gain, yellowness index and color difference results following the procedure of SAMPLE TESTING.

TABLE IV

| Run no. | Tensile at 300% elongation (MPa) | Tensile at break (MPa) | Elongation at break (%) | Weight gain (%) | Yellowness index before | Yellowness index after | Color difference before/background | Color difference after/before |
|---|---|---|---|---|---|---|---|---|
| 1 | 5.8 | 5.9 | 310 | 0.62 | — | — | — | — |
| 2 | — | 7.2 | 220 | 0.67 | — | — | — | — |
| 3 | — | 9.7 | 210 | 0.73 | — | — | — | — |
| 4 | 5.5 | 7.0 | 400 | — | — | — | — | — |
| 5 | 9.1 | 11.5 | 390 | 0.44 | — | — | — | — |
| 6 | 12.5 | 14.5 | 390 | 0.55 | 14.84 | 21.39 | 11.35 | 5.18 |
| 7 | 15.2 | 15.4 | 300 | 0.63 | — | — | — | — |
| 8 | — | 22.6 | 170 | 1.07 | — | — | — | — |
| 9 | — | — | — | 1.84 | — | — | — | — |
| 10 | — | — | — | 2.86 | — | — | — | — |
| 11 | 7.2 | 10.6 | 420 | 0.44 | — | — | — | — |
| 12 | 10.0 | 12.9 | 390 | 0.35 | 12.5 | 18.47 | 9.5 | 4.49 |
| 13 | 12.9 | 13.9 | 330 | 0.48 | — | — | — | — |
| 14 | 4.5 | 5.9 | 570 | 0.22 | — | — | — | — |
| 15 | 6.5 | 7.4 | 440 | 0.51 | — | — | — | — |
| 16 | 8.9 | 9.4 | 370 | 0.64 | — | — | — | — |
| 17 | 7.9 | 12.3 | 450 | 0.39 | 8.88 | 16.25 | 7.98 | 5.3 |
| 18 | 11.2 | 13.5 | 380 | 0.45 | — | — | — | — |
| 19 | 14.8 | 16.9 | 360 | 0.65 | — | — | — | — |
| 20 | 6.8 | 9.5 | 510 | 0.34 | — | — | — | — |
| 21 | 8.8 | 10.9 | 410 | 0.66 | — | — | — | — |
| 22 | 11.8 | 15.3 | 410 | 0.74 | 11.12 | 15.26 | 11.87 | 3.2 |
| 23 | 10.8 | 12.7 | 360 | 0.34 | — | — | — | — |
| 24 | 13.2 | 13.2 | 300 | 0.50 | — | — | — | — |
| 25 | — | 11.7 | 200 | 0.78 | — | — | — | — |
| 26 | 6.1 | 6.2 | 310 | 0.44 | — | — | — | — |
| 27 | 7.6 | 7.7 | 310 | 0.60 | — | — | — | — |
| 28 | — | 8.5 | 210 | 0.79 | — | — | — | — |
| 29 | — | 7.0 | 140 | — | 23.72 | 33.41 | 14.35 | 6.96 |
| 30 | 8.5 | 14.3 | 440 | — | — | — | — | — |
| 31 | — | — | — | — | 6.26 | 15.76 | 6.02 | 6.74 |
| 32 | — | — | — | — | 7.03 | 15.56 | 6.01 | 6.34 |
| 33 | — | — | — | — | 6.99 | 23.21 | 6.78 | 12.60 |
| 34 | — | — | — | — | 15.94 | 36.12 | 12.3 | 16.14 |
| 35 | — | — | — | — | 4.38 | 42.79 | 4.03 | 31.25 |
| 36 | — | — | — | — | 10.33 | 22.64 | 8.69 | 9.12 |
| 37 | — | — | — | — | 11.17 | 24.65 | 9.22 | 9.71 |
| 38 | — | — | — | — | 10.86 | 34.17 | 8.63 | 17.94 |
| 39 | — | — | — | — | 15.88 | 44.86 | 13.58 | 22.19 |
| 40 | — | — | — | — | 2.85 | 46.71 | 3.37 | 34.93 |
| 41 | — | — | — | — | 30.46 | 35.92 | 21.74 | 3.72 |
| 42 | — | — | — | — | 31.76 | 36.61 | 20.78 | 3.95 |
| 43 | — | — | — | — | 0.50 | 30.97 | 8.9 | 23.40 |
| 44 | — | — | — | — | 31.14 | 49.02 | 19.3 | 15.88 |
| Comparison 1 | 15.9 | 49.5 | >450 | 1.61 | 11.09 | 48.95 | 7.98 | 33.00 |
| Comparison 2 | 9.7 | 33.1 | 500 | 1.65 | 8.68 | 49.4 | 6.46 | 35.64 |

The data show that the materials that were tested for mechanical properties exhibited satisfactory mechanical properties, except run 29 which broke at 140% elongation. The weight gain values that were obtained for runs 1–44 were very satisfactory compared to the comparison materials, except runs 9 and 10 (which contained very high hard segment contents of 73% and 100% respectively). The materials of runs 1–44 that were tested for color difference exhibited significantly lower color difference values than the comparison materials except for runs 35 and 40 (which contained soft segment contents of 100% polyester and polyether respectively).

EXAMPLE 4

Preparation of Thermoset Polyurethanes

Thermoset polyurethanes with varying percentages of hard and soft segments were prepared by placing the respective amounts of diols listed in TABLE V in a vessel. An additional diol "TMP" (2-ethyl-2-(hydroxymethyl)-1,3-propanediol, Aldrich Chemical Co.) was added to Run nos. 4, 5 and 6 in amounts of 0.99%, 2.96% and 3.89% respectively. 0.49 Percent each TINUVIN 328 and TINUVIN 770 (except Run nos. 10, 12 and 17 where 0.46% was added, Run nos. 11 and 14 where 0.42% was added and Run no. 13 where 0.41% was added) and 0.10% MEHQ (except Run nos. 10, 12 and 17 where 0.09% was added, and Run nos. 11, 13 and 14 where 0.08% was added) were added to the vessel. The vessels were sealed and placed in a 100° C. oven for 5–10 minutes or until the additives melted. Each vessel was removed from the oven and allowed to cool to room temperature. Next, the amount of methylene bis(4-cyclohexylisocyanate) set out in TABLE V was added.

An additional isocyanate was added to Run nos. 7–17. DESMODUR N-100 (200 g/equivalent weight, Mobay Corp.) was added to Run nos. 7 and 10 at 0.99%, Run no. 11 at 1.6%, Run no. 8 at 2.96%, Run nos. 9 and 12 at 4.94%, Run no. 13 at 7.69%, Run no. 14 at 12.72%, Run no. 15 at 22.82% and Run no. 16 at 30.69%. 4.94 Percent DESMODUR N-3300 (195 g/equivalent weight, Mobay Corp.) was added to Run no. 17.

The mixture was stirred until it was homogeneous. Then 0.13% COTIN 222 was added to the vessel (except for Run nos. 11, 13 and 14 where 0.11% was added, Run nos. 10, 12 and 17 where 0.12% was added and Run nos. 1–3 where 0.17% was added).

Set out below in Table V are the type and amount of poly(butadiene)diol, 1,4-butanediol and methylene bis(4-cyclohexylisocyanate) in each mixture and the ratio of hard segment to soft segment for each polyurethane.

films were cut into strips measuring about 1.3 cm ×10 cm ×0.5 mm thick.

For comparative purposes, a commercially available thermoset polyurethane ("Comparison"), Compound E417-00 (Acushnet Company), was obtained in film form from the manufacturer. This film was cut into strips which were about 0.5 cm ×10 cm ×2 mm thick.

All of the samples were tested for tensile strength at 300% elongation, tensile strength at break and elongation at break,

TABLE V

| | Ingredients | | | |
|---|---|---|---|---|
| | Diol | | Methylene bis- | Ratio |
| | Poly(butadiene) | 1,4- | (4-cyclohexyl- | Hard:soft |
| Run no. | Type | Amount (%) | butanediol (%) | isocyanate) (%) | Segment (%):(%) |
|---|---|---|---|---|---|
| 1 | R-45HT[1] | 63.96 | 7.02 | 27.76 | 35:65 |
| 2 | R-45M[2] | 63.98 | 7.34 | 27.43 | 35:65 |
| 3 | PBD(2800)[3] | 63.96 | 7.19 | 27.59 | 35:65 |
| 4 | PBD(2000)[4] | 74.09 | 2.93 | 20.78 | 25:75 |
| 5 | " | 74.09 | 0.92 | 20.81 | 25:75 |
| 6 | " | 74.09 | 0.00 | 20.81 | 25:75 |
| 7 | " | 74.09 | 3.82 | 19.89 | 25:75 |
| 8 | " | 74.09 | 3.69 | 18.04 | 25:75 |
| 9 | " | 74.09 | 3.52 | 16.23 | 25:75 |
| 10 | PBD(G2000)[5] | 69.20 | 5.28 | 23.39 | 30:70 |
| 11 | " | 68.84 | 5.20 | 23.32 | 30:70 |
| 12 | " | 69.20 | 4.91 | 19.80 | 30:70 |
| 13 | " | 67.27 | 4.75 | 19.28 | 32:68 |
| 14 | " | 69.25 | 4.21 | 12.78 | 30:70 |
| 15 | " | 74.09 | 1.88 | 0.00 | 25:75 |
| 16 | " | 63.98 | 4.12 | 0.00 | 35:65 |
| 17 | " | 69.20 | 4.91 | 19.80 | 30:70 |

[1]2,800 M.W. hydroxyl-terminated poly(butadiene), hydroxyl functionality of 2.4 to 2.6 (Atochem, Inc.).
[2]2,800 M.W. hydroxyl-terminated poly(butadiene), hydroxyl functionality of 2.2 to 2.4 (Atochem, Inc.).
[3]2,800 M.W. hydroxyl-terminated poly(butadiene) (Aldrich Chemical Co.).
[4]2,000 M.W. hydroxyl-terminated poly(butadiene) (Polysciences Inc.).
[5]2,000 M.W. hydroxyl-terminated poly(butadiene) (Nissho Iwai American Corp.).

Each reaction mixture was stirred vigorously until slight exotherm was observed and then immediately poured into the mold cavity of mold assembly A treated with mold release agent RAM 225 (RAM Products). The mixture was covered with a sheet of SCOTCHPAK polyester film (3M) followed by the mold coverpiece. The mold assembly was then placed in a press (P. H. I. Press, Pasadena Hydraulics, Inc.) at an indicated force of 18,000 kg and with a platen temperature of 110° C. for about 30 minutes. The resultant and the results are set out in TABLE VI. Weight gain as reported in Table VI was measured by preparing film samples and carrying out moisture uptake testing as detailed in SAMPLE TESTING, except that the sample size for the comparison material was about 0.5 cm ×0.5 cm ×2 mm thick. Table VI also provides the results of yellowness index and color difference testing which,was carried out using the film sizes (except for Compound E417-00) and procedures as set out in SAMPLE TESTING.

TABLE VI

| Run no. | Tensile at 300% elongation (MPa) | Tensile at break (MPa) | Elongation at break (%) | Weight gain (%) | Yellowness index before | Yellowness index after | Color difference before/ background | Color difference after/before |
|---|---|---|---|---|---|---|---|---|
| 1 | 13.7 | 13.7 | 300 | 0.63 | 12.09 | 24.18 | 14.38 | 9.15 |
| 2 | 8.8 | 9.2 | 310 | 0.58 | 16.74 | 29.08 | 18.74 | 9.52 |
| 3 | 9.9 | 11.9 | 360 | 0.73 | 25.09 | 34.12 | 28.39 | 7.09 |
| 4 | 12.3 | 13.0 | 300 | 0.63 | 4.64 | 10.8 | 5.71 | 4.66 |
| 5 | — | 12.2 | 200 | 0.62 | — | — | — | — |
| 6 | — | 12.1 | 170 | 0.43 | 2.63 | 8.73 | 3.71 | 4.23 |
| 7 | 10.1 | 11.4 | 330 | — | — | — | — | — |
| 8 | 9.0 | 9.2 | 310 | — | — | — | — | — |
| 9 | — | 5.0 | 250 | — | — | — | — | — |
| 10 | — | — | — | — | — | — | — | — |
| 11 | 15.8 | 16.5 | 305 | 0.62 | — | — | — | — |

TABLE VI-continued

| Run no. | Tensile at 300% elongation (MPa) | Tensile at break (MPa) | Elongation at break (%) | Weight gain (%) | Yellowness index before | Yellowness index after | Color difference before/ background | Color difference after/before |
|---|---|---|---|---|---|---|---|---|
| 12 | — | — | — | — | — | — | — | — |
| 13 | 15.6 | 15.6 | 300 | 0.81 | — | — | — | — |
| 14 | — | — | — | — | 5.05 | 19.09 | 7.21 | 9.59 |
| 15 | — | — | — | — | — | — | — | — |
| 16 | — | — | — | — | — | — | — | — |
| 17 | — | — | — | — | 5.14 | 13.25 | 6.06 | 5.57 |
| Comparison | 12.6 | 18.5 | 440 | 1.23 | 11.7 | 57.4 | 11.01 | 40.68 |

The data show that the thermoset polyurethanes exhibit very satisfactory tensile strength at 300% elongation, tensile strength at break and an elongation at break of greater than 150%. Also, the weight gain values obtained for runs 1–17 were considerably less than that of the comparison material. The thermoset polyurethanes of runs 1–17 that were immersed in mustard show very good resistance to staining by mustard, while the comparison thermoset polyurethane showed much less resistance to staining by mustard.

EXAMPLE 5

Preparation of Radiation Crosslinked Polyurethanes

Three radiation-crosslinkable polyurethanes were prepared by placing 73.87% 2,000 molecular weight hydroxyl-terminated poly(butadiene)diol (Polysciences Inc.) in a vessel with 1,4 butanediol and 2-glyceryl methacrylate in the amounts set out in Table VII. 0.49 Percent each TINUVIN 328 and TINUVIN 770, 0.10% MEHQ and 0.30% photoinitiator benzyl methyl ether were added to the vessel. The vessels were sealed and placed in a 100° C. oven for 5–10 minutes or until additives melted. Each vessel was removed from the oven. The amount of methylene bis(4-cyclohexylisocyanate) set out in TABLE VII was added and the mixture stirred until it was homogeneous. Then 0.13% COTIN 222 was added to each vessel.

Set out below in Table VII are the amounts of 1,4-butanediol, 2-glyceryl methacrylate and methylene bis(4-cyclohexylisocyanate) in each mixture. The ratio of hard segment to soft segment for each polyurethane was 25 to 75.

TABLE VII

| Run no. | 1,4-butanediol (%) | 2-Glyceryl methacrylate (%) | Methylene bis-(4-cyclohexyl-isocyanate) (%) |
|---|---|---|---|
| 1 | 3.25 | 0.98 | 20.39 |
| 2 | 1.90 | 2.95 | 19.76 |
| 3 | 0.59 | 4.92 | 19.11 |

Each reaction mixture was stirred until slight exotherm was observed and the viscosity of the mixture noticeably increased. Each mixture was then poured into a polytetrafluoroethylene-lined aluminum pan and cured in a 100° C. oven for about 30 minutes. Next, each mixture was pressed into a film using mold assembly A and the Wabash press. The press platens were held at 165° C. for 3 minutes at a force of 1,000 kg, then at 11,000 kg for 8 minutes, followed by cooldown at 11,000 kg for 8 minutes. The material was then crosslinked by passing it through a UV processor (RPC Industries), with the lamp setting on normal (i.e., both lamps on), under a nitrogen atmosphere and at 15.2 meters per minute such that the material received 0.65 joules/sec-cm$^2$.

The prepared films were cut into strips of about 1.3 cm ×10 cm ×0.5 mm thick and were tested for tensile strength at 300% elongation, tensile strength at break and elongation at break. The results are set out in TABLE VIII along with the results of yellowness index and color difference after/before testing (which were conducted using the thicker film samples and procedures set out in SAMPLE TESTING). Color difference before/background for Run nos. 1 and 3 was 19.22 and 19.33 respectively.

TABLE VIII

| Run no. | Tensile at 300% elongation (MPa) | Tensile at break (MPa) | Elongation at break (%) | Yellowness index before | Yellowness index after | Color difference after/before |
|---|---|---|---|---|---|---|
| 1 | 9.0 | 10.8 | 350 | 20.35 | 27.72 | 5.45 |
| 2 | 7.7 | 8.3 | 310 | — | — | — |
| 3 | — | 6.9 | 260 | 27.26 | 33.48 | 4.39 |

The data show that the three radiation crosslinked polyurethanes exhibit satisfactory mechanical properties and very satisfactory resistance to staining.

EXAMPLE 6

Preparation of Silicones

The following silicone polymers were molded into films:

Run no. 1. α-Methyl styrene-silicone-α-methyl styrene block copolymer—Resin X-4-2518 (Dow Corning), Run no. 2. α-Methyl styrene-silicone-α-methyl styrene block copolymer—Resin X-4-2541 (Dow Corning), Run no. 3. Two part silicone elastomeric material PEM 25A and PEM 25B (Petrarch Systems), and Run no. 4 Silicone polycarbonate (General Electric).

Silicone polymers of Run nos. 1, 2 and 4 were made into films using mold assembly A and the Wabash press. The press platens were held at 180° C. for 3 minutes at 1,000 kg, 180° C. for 8 minutes at 12,500 kg, then cooled at 12,500 kg.

The two part silicone elastomer of Run no. 3 was made into a film by placing 10 parts Clean Grade Liquid Silicone Elastomer PEM 25A and 1 part Clean Grade Liquid Silicone Elastomer PEM 25B (both Lot #80276 from Petrarch Systems, Inc.) in a vessel and stirring until a homogeneous mixture was obtained. The mixture was then placed in mold assembly A, placed in the P. H. I. press described in EXAMPLE 4 at room temperature and at an indicated force of 18,000 kg for 2 hours to eliminate bubbles from the sample. The mold assembly was removed from the press and the materials were allowed to continue curing at ambient conditions for 2 to 3 days.

The prepared films of Run nos. 1–4 were cut into strips of about 1.3 cm ×10 cm ×0.5 mm and tested for tensile strength at 300% elongation, tensile strength at break and elongation at break. The results are set out in TABLE IX along with yellowness index and color difference after/before results (which were obtained using the thicker films according to the procedures of SAMPLE TESTING). Color difference before/background for Run nos. 1–4 was 13.12, 6.52, 7.23 and 16.08 respectively.

TABLE IX

| Run no. | Tensile at 300% elongation (MPa) | Tensile at Break (MPa) | Elongation at break (%) | Yellowness index before | Yellowness index after | Color difference after/before |
|---|---|---|---|---|---|---|
| 1 | 8.7 | 8.8 | 310 | 9.38 | 12.11 | 1.92 |
| 2 | 3.9 | 5.2 | 520 | 6.46 | 8.57 | 1.60 |
| 3 | 1.9 | 2.5 | 370 | 4.54 | 7.63 | 2.02 |
| 4 | — | 11.2 | 180 | 13.71 | 23.23 | 7.57 |

The data show that the silicone materials of Runs 1–4 have a satisfactory tensile at break and elongation at break and exhibit very high resistance to staining by mustard.

EXAMPLE 7

Preparation of Thermoplastic Rubber Polymers

Four styrene-ethylene/butylene-styrene block copolymers, two styrene-butadiene-styrene block copolymers and one styrene-isoprene block copolymer (all KRATON materials from Shell Chemical Company and identified by the manufacturer's designations in Table X) were pressed into films for testing. The films of designations D1102, D1320X and D2103 were made with mold assembly A with the platen at 190° C. and 1,000 kg for 1 minute, 11,000 kg for 10 minutes, then cooldown at 11,000 kg for 8 minutes. Thicker films of each designation (as set out in SAMPLE TESTING) were made for stain resistance testing.

Films of designations G2701X, G2703X, G2706X and G2712X were made using an injection molding machine (ARBURG, Model "Allrounder 220E/150") with an aluminum mold having a polymer-receiving cavity of 3.9 cm ×12.5 cm ×2.5 mm. The injection speed setting was 5.0, the nozzle power setting was 35% and the screw speed was 360 RPM. For designation G2703X, the pressure was 35 kg/cm$^2$, the mold heater was 65° C., the back heater was 180° C. and the front heater was 190° C. For designation G2706X, the pressure was 50 kg/cm$^2$, the mold heater was 70° C., the back heater was 215° C. and the front heater was 230° C. For designation G2701X, the pressure was 40 kg/cm$^2$, the mold heater was 70° C., the back heater was 180° C. and the front heater was 190° C. The 'blue' timer (representing the time of injection and holding of the mold under heated conditions) was set at 15 seconds in each instance. The 'red' timer (which represents the total molding time and thus includes a cooldown time) was set at 17 seconds for designations G2701X and G2703X and 19 seconds for designations G2706X and G2712X.

Two other thermoplastic rubber polymers were also formulated and tested. The first formulation was a 50:50 blend of two styrene-ethylene/butylene-styrene block copolymers (KRATON G2703X and KRATON G1652). The second formulation was a blend of 90% styrene-ethylene/butylene-styrene block copolymer (KRATON G2703X) and 10% fumed silica (CAB-O-SIL TS-720, Cabot Corp.). Each formulation was blended in a bag as dry ingredients, then pellitized by placing the formulation in the inlet of a single screw extruder (PRODEX, model 7JX) having a mixing element in zones 3 and 4. The extruder conditions were: die temperature of 205° C.; zone temperatures 2 and 3 of 205° C., 3 and 4 of 190° C., 4 and 5 of 180° C., 6 of 160° C.; gear position #3, screw #5, screw speed 30 RPM, screw power 4.2 kg-calories/min., zone #1 pressure 350 kg/cm$^2$, and zone #1 melt temperature of 190° C. The formulations were molded into thick films using mold assembly C with the Wabash press platens held at 165° C. for 3 minutes at 1,000 kg, then for 8 minutes at 11,000 kg, then cooldown for 8 minutes at 11,000 kg.

Each film was tested for tensile strength at 300% elongation, tensile strength at break, elongation at break, yellowness index and color difference according to the procedure of SAMPLE TESTING, except that the films made using the injection molding machine were also used for yellowness index and color difference testing. The results are set out in Table X along with weight gain data.

TABLE X

| KRATON designation | Tensile at 300% elongation (MPa) | Tensile at break (MPa) | Elongation at break (%) | Weight gain (%) | Yellowness index before | Yellowness index after | Color difference before/ background | Color difference after/before |
|---|---|---|---|---|---|---|---|---|
| G2701X | 4.6 | 7.9 | >630 | — | 7.58 | 9.01 | 7.09 | 1.13 |
| G2703X | 4.3 | 8.1 | >570 | — | 13.03 | 16.27 | 11.82 | 1.89 |
| G2706X | 2.6 | 7.4 | >640 | 0.43 | 4.61 | 6.86 | 11.77 | 1.53 |
| G2712X | 2.6 | 5.7 | >640 | 0.58 | 7.82 | 10.96 | 6.72 | 2.4 |
| D1102 | 2.3 | 12.5 | >730 | — | 9.67 | 18.21 | 8.31 | 5.87 |
| D1320X | 0.6 | 2.1 | >810 | — | 8.42 | 18.28 | 10.67 | 6.37 |
| D2103 | 2.4 | 8.8 | >700 | — | 25.79 | 33.98 | 17.39 | 5.07 |
| G2703X/G1652 | — | — | — | — | 15.92 | 17.75 | 12.47 | 2.61 |
| G2703X/CABOSIL | — | — | — | — | 27.16 | 30.30 | 19.58 | 2.17 |

The data show that the KRATON materials are highly resistant to staining due to immersion in mustard. All of the KRATON films exhibit good mechanical properties, except D1320X. Also, the data show that the KRATON films have very little weight gain due to moisture uptake.

EXAMPLE 8

Preparation of EPDM Rubbers

The formulation of Run no. 1 was made by combining 700 parts ethylene propylene dimer terpolymer (NORDEL 1470, E. I. du Pont de Nemours & Co.), 420 parts mineral filler (TRANSLINK 37, Englehard Corp.), 21 parts polymerized quinoline antioxidant (AGERITE STALITE S, R. T. Vanderbilt), 7 parts zinc antioxidant (VANOX ZMTI, R. T. Vanderbilt), 35 parts zinc oxide (C. P. Hall), 280 parts high viscosity paraffin (SUNPAR 2280, Sun Oil Co.), 70 parts pure titanium dioxide (E. I. du Pont de Nemours & Co.), 56 parts amorphous fumed silica (CAB-O-SIL M7, Cabot Corp.) and 21 parts acrylate crosslinker (SR-206, Sartomer Co.). The ingredients were combined in a Banbury mixer (Farrel Birmingham, Buffalo, N.Y.) and mixed at room temperature for 5 minutes, during which time the reaction temperature reached 120°–150° C. The resultant mixture was removed from the mixer and allowed to cool to room temperature (i.e., about 25° C.).

The mixture was added along with 63 parts of dicumyl peroxide (DICUP 40KE, Hercules) to a two-roll mill having 30.5 cm rolls, and repeatedly passed through the nip between the rolls (with occasional cutting and folding of the mixture) at room temperature. The formulation of Run no. 2 was prepared in the same way as Run no. 1 except that the ethylene propylene dimer terpolymer was EPSYN 4506 (Copolymer Co.).

The resultant formulations were then cured using mold assembly B to press films according to the procedure of SAMPLE PREPARATION. For these formulations, the platen was held at 195° C.–200° C. at 1,000 kg for 1 minute, at 11,000 kg for 10 to 15 minutes, then at 11,000 kg during cooldown for 8 minutes. For mechanical testing, the films were cut into strips of 1.3 cm ×10 cm ×0.5 mm and soaked in mixed hexanes for 20 hours to separate the cured composition from the polyester films. The strips were again soaked in mixed hexanes for 20 hours, after which time they were air dried and tested for mechanical properties. For yellowness index and color difference testing, each formulation was pressed into a thick film using mold assembly C.

TABLE XI provides the mechanical, yellowness index and color difference testing results which were obtained according to the procedures of SAMPLE TESTING. The weight gain measured for Run no. 1 was 0.42%, while the weight gain for Run no. 2 was 0.51%. Color difference before/background was 12.94 and 14.16 for Run nos. 1 and 2 respectively.

TABLE XI

| Run no. | Tensile at 300% elongation (MPa) | Tensile at Break (MPa) | Elongation at break (%) | Yellowness index before | Yellowness index after | Color difference after/before |
|---|---|---|---|---|---|---|
| 1 | 2.4 | 7.6 | >720 | 22.39 | 34.18 | 7.78 |
| 2 | 2.8 | 7.9 | >720 | 22.09 | 29.06 | 4.31 |

The data show that the EPDM materials set out above provide substantial elongation at break and exhibit satisfactory resistance to staining by mustard.

EXAMPLE 9

Preparation of Fluoroelastomers

The nine formulations of TABLE XII (set out in parts) were prepared by adding the triallyl isocyanurate to the silica and then blending these ingredients with the remaining ingredients to form a dry mix. Each mix was added to a two-roll mill, and repeatedly passed through the nip between the rolls (with occasional cutting and folding) at room temperature for 10–15 minutes or until it was thoroughly mixed.

TABLE XII

| Ingredient | Run no. | | | | | | | | |
|---|---|---|---|---|---|---|---|---|---|
| | 1 | 2 | 3 | 4 | 5 | 6 | 7 | 8 | 9 |
| Fluoropolymer[1] | 100 | 100 | 100 | 100 | 100 | 100 | 100 | 100 | 100 |
| Fumed silica[2] | 15 | 15 | 15 | 23 | 15 | 15 | 15 | 15 | 15 |
| Isocyanurate[3] | 3 | 3 | 4 | 4 | 1.5 | 0.75 | 0.75 | 0.75 | 0.75 |
| Peroxide[4] | 2.5 | 2.5 | 1.25 | 1.25 | 0.75 | 0.37 | 0.37 | 0.37 | 0.37 |
| Butanediol diglycidyl ether[5] | 1.0 | 1.0 | 1.0 | 1.0 | 1.0 | 1.0 | 1.0 | 1.0 | 1.0 |
| Polytetrafluoroethylene[6] | 0 | 10 | 10 | 10 | 0 | 0 | 10 | 0 | 0 |
| Titanium dioxide[7] | 0 | 0 | 0 | 0 | 0 | 0 | 0 | 1.0 | 0 |
| Zinc sulfide[8] | 0 | 0 | 0 | 0 | 0 | 0 | 0 | 0 | 1.0 |

[1]FLS 2690 (3M).
[2]AEROSIL R-972 (Degussa Corp.).
[3]Triallyl isocyanurate (Mitsubishi Corp.).
[4]Run nos. 1–2, LUPERCO 101-XL; Run nos. 3–9, LUPERSOL 101 (both from Pennwalt).
[5]ARALDITE RD2 (Ciba Products Co.).
[6]Run Nos. 3, 4 and 7, TEFLON MP 1000; Run No. 2, TEFLON MP 1500 (both from E. I. du Pont de Nemours & Co.).
[7]UNITANE (American Cyanimide).
[8](C. P. Hall).

Two fluorosilicone resins were obtained and molded into films. One percent 2,5-dimethyl-2,5-bis-(t-butylperoxy)hexane (LUPERCO 101XL) was independently combined in a two roll mill with 99% fluorosilicone resins FE251U and FE351U (both Shin-Etsu Chemical Co.) to provide the formulations of Runs 10–11 respectively. Each formulation was passed through the nip between the rolls of a two-roll mill (with occasional cutting and folding) at room temperature for 10–15 minutes until it was thoroughly mixed.

Each formulation of TABLE XII and the two fluorosilicone resin formulations were pressed into films by placing about 100 grams of each formulation in two 15 cm ×15 cm ×1.9 mm cavities of a 25 cm ×36 cm ×1.2 cm mold assembly base plate. Each cavity was surrounded by a flash groove. A 25 cm ×36 cm ×1.2 cm top plate was placed over the base plate, and the assembly was placed between 20.3 cm diameter rams of the Wabash press. The platens were held at 175° C. for 10 minutes at 50,000 kg to form the films for Run nos. 1–9, and at 165° C. for 10 minutes at 50,000 kg to form the films of Run nos. 10–11. For Run nos. 10–11 only, the films were postcured in a 200° C. oven for 4 hours.

The fluoroalkoxyphosphazene material of Run no. 12 (EXPEL-F, Compound X-122B, Ethyl Corp.) was obtained in film form from the manufacturer.

The films were cut into strips, each about 0.3 to 0.6 cm ×6 cm ×2 mm thick and tested for tensile strength at 300% elongation, tensile strength at break, elongation at break, yellowness index and color difference according to SAMPLE TESTING. The results, along with weight gain data, are provided in TABLE XIII.

TABLE XIII

| Run no. | Tensile at 300% elongation (MPa) | Tensile at break (MPa) | Elongation at break (%) | Weight gain (%) | Yellowness index before | Yellowness index after | Color difference before/ background | Color difference after/before |
|---|---|---|---|---|---|---|---|---|
| 1 | 13.1 | 14.2 | 320 | 0.65 | 6.78 | 4.19 | 20.86 | 1.10 |
| 2 | 13.6 | 14.1 | 310 | 0.60 | 8.10 | 7.39 | 22.56 | 0.32 |
| 3 | 14.2 | 14.3 | 300 | 0.50 | 6.93 | 12.15 | 18.99 | 2.51 |
| 4 | — | 17.1 | 240 | 0.46 | 8.32 | 10.40 | 29.49 | 1.11 |
| 5 | 14.1 | 14.9 | 310 | — | 37.01 | 37.19 | 19.23 | 0.32 |
| 6 | 7.5 | 12.6 | 410 | — | 25.6 | 24.08 | 19.18 | 0.93 |
| 7 | 11.8 | 13.0 | 330 | — | 22.77 | 21.47 | 17.03 | 0.82 |
| 8 | 9.7 | 12.7 | 360 | — | 11.82 | 12.28 | 5.93 | 0.4 |
| 9 | 10.0 | 12.6 | 360 | — | 10.33 | 11.19 | 4.76 | 0.54 |
| 10 | 7.0 | 9.2 | 360 | — | 32.17 | 31.08 | 14.52 | 1.84 |
| 11 | 7.0 | 12.3 | 410 | — | 35.75 | 37.29 | 23.68 | 1.60 |
| 12 | — | 9.2 | 150 | — | 29.31 | 32.74 | 26.01 | 1.74 |

The data show that these fluoroelastomers are highly resistant to staining by mustard, and also exhibit excellent mechanical properties. The data also show that these materials gain little weight due to moisture uptake.

We claim:

1. An elastomeric orthodontic force module that is sufficiently free of hydrocarbon-based polyether segments and hydrocarbon-based polyester segments to provide resistance to staining, said force module being made of a material having per 2 mm thickness a Hunter color difference when using a 2.5 cm illuminated opening of (a) less than 40 when compared to a Hunter white standard tile and (b) less than 33 after immersion in mustard solution for 30 minutes when compared to the material before immersion in mustard solution, said material comprising silicone polymer, wherein said force module at room temperature can be repeatedly stretched to twice its original length and will forcibly return to approximately its original length after removal of a tensile stress.

2. The force module of claim 1, wherein said material has per 2 mm thickness a Hunter color difference when using a 2.5 cm illuminated opening of less than 30 when compared to a Hunter white standard tile.

3. The force module of claim 1, wherein said material comprises a crosslinked silicone elastomer.

4. The force module of claim 1, wherein said material comprises an α-methyl styrene-silicone-α-methyl styrene block copolymer.

5. The force module of claim 1, wherein said material comprises a silicone polycarbonate block copolymer.

6. The force module of claim 2, wherein said material has per 2 mm thickness a Hunter color difference when using a 2.5 cm illuminated opening of less than 20 when compared to a Hunter white standard tile.

7. The force module of claim 6, wherein said material can be stretched to at least 150% elongation without breakage.

8. The force module of claim 2, wherein said material has per 2 mm thickness a Hunter color difference when using a 2.5 cm illuminated opening of less than 20 after immersion in mustard solution for 30 minutes when compared to the material before immersion in mustard solution.

9. The force module of claim 2, wherein said material has per 2 mm thickness a Hunter color difference when using a 2.5 cm illuminated opening of less than 10 after immersion in mustard solution for 30 minutes when compared to the material before immersion in mustard solution.

10. The force module of claim 2, wherein said material can be stretched to at least 150% elongation without breakage.

11. The force module of claim 2, wherein said material can be stretched to at least 300% elongation without breakage.

12. The force module of claim 2, wherein said material has a tensile strength of greater than 2.0 MPa at 300% elongation.

13. The force module of claim 2, wherein said material has a tensile strength of greater than 4.0 MPa at 300% elongation.

14. The force module of claim 2, wherein said material has a tensile strength in the range of 2.0 MPa to 30 MPa at 300% elongation.

15. The force module of claim 2, wherein said material has a tensile strength of less than 30 MPa at 300% elongation.

16. The force module of claim 2, wherein said force module is a ligature.

17. The force module of claim 16, wherein said ligature includes a bumper portion.

18. The force module of claim 2, wherein said force module is an elongated module having opposed, annular terminal end portions.

19. The force module of claim 18, wherein said terminal end portions are interconnected by a flexible shaft portion.

20. The force module of claim 18, wherein said terminal end portions are interconnected by additional annular portions.

21. The force module of claim 2, wherein said force module is a tooth separator.

22. The force module of claim 2, wherein said force module is a rotation wedge.

23. The force module of claim 1, wherein said material has per 2 mm thickness a Hunter color difference when using a 2.5 cm illuminated opening of (a) less than 20 when compared to a Hunter white standard tile and (b) less than 20 after immersion in mustard solution for 30 minutes when compared to the material before immersion in mustard solution.

24. The force module of claim 23, wherein said material has a tensile strength in the range of 2.0 MPa to 30 MPa at 300% elongation.

25. The force module of claim 1, wherein said material has per 2 mm thickness a Hunter color difference when using a 2.5 cm illuminated opening of (a) less than 20 when compared to a Hunter white standard tile and (b) less than 10 after immersion in mustard solution for 30 minutes when compared to the material before immersion in mustard solution.

26. The force module of claim 25, wherein said material has a tensile strength in the range of 2.0 MPa to 30 MPa at 300% elongation.

27. The force module of claim 1, wherein said material can be stretched to at least 300% elongation without breakage.

28. The force module of claim 1, wherein said material has a tensile strength in the range of 2.0 MPa to 30 MPa at 300% elongation.

29. The force module of claim 1, wherein said material has a tensile strength of greater than 4.0 MPa at 300% elongation.

* * * * *

UNITED STATES PATENT AND TRADEMARK OFFICE
CERTIFICATE OF CORRECTION

PATENT NO. : 5,461,133

DATED : October 24, 1995

INVENTOR(S) : W. James Hammar and Miriam D. Nave

It is certified that error appears in the above-indentified patent and that said Letters Patent is hereby corrected as shown below:

Col. 3, line 58, "G270X" should read --G2703X--

Col. 4, line 59, delete the comma after -- These --.

Col. 5, line 31, delete the hyphen after -- EPM --.

Col. 5, line 42, add a hyphen after "per".

Col. 9, line 12, add an asterisk after "b".

Col. 9, line 45, "8" should read -- 68 --.

Col. 16, line 27, "60" should read -- 660 --.

Signed and Sealed this

Eighteenth Day of February, 1997

Attest:

BRUCE LEHMAN

Attesting Officer

Commissioner of Patents and Trademarks